United States Patent [19]
Oremland et al.

[11] Patent Number: 6,013,254
[45] Date of Patent: Jan. 11, 2000

[54] METHOD FOR ENHANCING OXIDATION OF METHYL BROMIDE WITH STRAIN IMB-1 (ATCC 202197) DURING AGRICULTURAL FUMIGATIONS

[75] Inventors: Ronald S. Oremland, San Francisco; Tracey L. Connell, Santa Cruz; Laurence G. Miller, El Granada, all of Calif.

[73] Assignee: The United States of America as represented by the Secretary of the Interior, Washington, D.C.

[21] Appl. No.: 09/093,341

[22] Filed: Jun. 9, 1998

[51] Int. Cl.[7] .......................... A01N 25/00; A01N 63/00; B09B 3/00; C12N 1/00
[52] U.S. Cl. ........................ 424/93.4; 210/601; 424/405; 435/262.5; 435/822; 435/878
[58] Field of Search .................................. 424/93.4, 405; 435/262.5, 822, 878; 210/601

[56] References Cited

U.S. PATENT DOCUMENTS 5,753,183  5/1998  Ohr et al. .................................. 422/37

OTHER PUBLICATIONS

Connell et al., "Bact. oxid. of MBr" Env. Sci. & Tech. 31(5)1997, pp. 1489–1495; abstr. only.

*Primary Examiner*—David M. Naff
*Assistant Examiner*—Deborah K. Ware
*Attorney, Agent, or Firm*—E. Philip Koltos

[57] ABSTRACT

A method is provided for enhancing oxidation of methyl bromide during agricultural fumigations of fields using a fumigant containing methyl bromide. The method comprises adding a methylotrophic bacterium to the soil in an amount effective to provide bacterial oxidation of the methyl bromide. The bacterium preferably comprises a bacterium isolated from agricultural soil, and, in a specific embodiment, comprises a 16S ribosomal RNA gene sequence in the Alpha subgroup of Proteobacteria designated strain IMB-1 (ATCC 202197). The fumigant also includes chloropicrin in an amount reduced to a level which permits said bacterial oxidation but while still enables the chloropicrin to serve as a warning agent for excessive release of methyl bromide from the soil. The soil can be pretreated with methyl iodide. The bacterium is applied to the soil as freeze-dried bacterial cells during the fumigation operation.

8 Claims, No Drawings

METHOD FOR ENHANCING OXIDATION OF METHYL BROMIDE WITH STRAIN IMB-1 (ATCC 202197) DURING AGRICULTURAL FUMIGATIONS

FIELD OF THE INVENTION

The present invention relates to a method for controlling emissions of methyl bromide (MeBr) into the atmosphere after the application thereof to fumigated fields.

BACKGROUND OF THE INVENTION

MeBr is a soil fumigant that has been extensively used throughout the world for the elimination of pests (e.g., nematodes, fungi) during the cultivation of a wide variety of vegetables, specialty fruit (i.e., strawberries) and flowers. Typically, MeBr is added to soils in conjunction with chloropicrin ("tear gas") to enhance toxicity and to serve as a warning agent. A tarp is used to cover the area to which the MeBr is applied.

Because MeBr has a relatively long tropospheric residence time (currently the subject of scientific debate but generally accepted to be between 0.7 and 1.8 years), some portion of the atmospheric burden will be transported up to the stratosphere and participate in a series of reactions which result in the destruction of the Earth's protective ozone layer. Because molecules of bromine are about 50-fold more efficient at destroying ozone than molecules of chlorine, MeBr has become a focus of an addenda to the Montreal Protocol of 1991, which calls for an international phasing out of the use of MeBr over the next fifteen years. It is noted that natural sources of MeBr account for most of the emissions to the atmosphere, while agricultural fumigations appears to account for 16–33%. Nonetheless, this phase-out of MeBr, which will be accelerated in the United States due to implementation of the Clear Air Act (2001), will deprive food growers of a very useful, non-residue accumulating pesticide.

Methods for combating the problems associated with using MeBr as a fumigant include physical manipulations, such as soil compaction and deeper injection of MeBr, with the purpose of increasing the retention of MeBr within the soil, thereby providing more extensive degradation and a subsequent decrease in the outward flux thereof to the atmosphere. In addition, the use of thicker, impermeable covering tarps has been proposed to reduce MeBr losses to the atmosphere. Another approach is to use methyl iodide rather than MeBr because of the very short atmospheric residence time thereof, and reference is made in this regard to U.S. Pat. No. 5,518,692 to Grech et al. for a discussion of this approach as well as the general problem under consideration. Methyl iodide has different physical properties from MeBr and may not be as effective in destroying crop pests, and, in any event, is substantially more expensive. Reference is also made to U.S. Pat. No. 4,664,805 to Focht which relates to a method for accelerating the decontamination of an environment contaminated with toxic halogenated organic compounds (MeBr is one of very many examples) by adding both (1) microorganisms which are not indigenous to the environment and (2) a non-toxic analog of the halogenated organic compound.

A clear need exists for a way to use MeBr in the fumigation of fields which would satisfy the different needs and requirements of growers, fumigators, environmentalists and various world and U.S. Agencies and local governments and, more particularly, for a method or way of applying MeBr in fumigating fields so that the MeBr can function to eliminate crop pests, but would not emitted to the atmosphere over the periods of tarping operations (about 6 days).

SUMMARY OF THE INVENTION

In accordance with the invention, a method is provided for reducing or eliminating the emission of MeBr from fumigated soils, thereby permitting continued use of the important chemical while protecting stratospheric ozone.

According to the method of the invention, oxidation of methyl bromide is enhanced during agricultural fumigations of fields growing in soils using a fumigant containing methyl bromide, by adding a methylotrophic bacterium to the soil in an amount effective to provide bacterial oxidation of the methyl bromide.

Preferably, the bacterium comprises a bacterium isolated from agricultural soil and more preferably, the bacterium comprises a 16S ribosomal RNA gene sequence in the alpha subgroup of Proteobacteria referred to as strain IMB-1. A deposit of microorganism strain IMB-1 was made on Feb. 12, 1999, under the terms of the Budapest Treaty with the American Type Culture Collection of 10801 University Blvd., Manassas, Va. 20110-2209; and the accession number assigned is ATCC 202197.

As mentioned above, the fumigant characteristically includes chloropicrin in addition to MeBr and in accordance with a further aspect of the invention, the amount of chloropicrin is reduced to a level which permits the aforesaid bacterial oxidation while enabling the chloropicrin to still serve as warning agent.

In accordance with a further feature of the invention, the soil being fumigated is preferably pretreated with methyl iodide.

Advantageously, the bacterium used is applied to the soil as freeze-dried bacterial cells during the fumigation of operation. The bacterium is preferably prepared by mass culturing. In one embodiment, the mass culturing uses glucose or methylamine as a substrate.

Other features and advantages of the invention will be set forth in, or apparent from, the detailed description of the preferred embodiments of the invention which is found hereinbelow.

DESCRIPTION OF THE PREFERRED EMBODIMENTS

The invention is the product of research concerned with development of an understanding as to what types of microbes are capable of destroying MeBr, research based on the conviction that the process is a biological one rather than a chemical reaction. It has been discovered that soil bacteria, or bacteria isolated from soils, can be used for this purpose and that, among these, a facultative methylotrophic bacterium, strain IMB-1, isolated from agricultural soil, can be used for this purpose.

Strain IMB-1 grows on MeBr as well as methyl iodide, methyl chloride, methylated amines and also on glucose, pyrurate or acetate. Phylogenetic analysis of the 16S ribosomal RNA gene sequence of strain IMB-1 indicates that the strain is classifiable in the Alpha subgroup of the Proteobacteria. An important characteristic of this strain is the ability thereof to oxidize MeBr and this ability is constitutive in cells regardless of the growth substrate.

Considering the morphology and phylogeny of strain IMB-1, strain IMB-1 is a motile, gram-negative rod (dimensions~1.3×0.6 $\mu$m). A phylogenetic tree generated from comparisons of the 16S ribosomal RNA gene sequences classifies strain IMB-1 in the Alpha subgroup of the Proteobacteria, as stated above. Strain IMB-1 is not closely related to recognized strains of methanotrophs or of methanol-utilizers but rather is more related to soil nitrogen-fixing bacteria of the genus Rhizobium. It is most closely related to strain ER2, a methylotroph which degrades methylcarbamate insecticides.

Strain IMB-1 has been shown to grow using MeBr as a sole source of carbon and energy. Growth was also obtained when methyl iodide served as the electron donor, and iodide accumulated in the medium as a consequence of this growth. However, only about one third of the methyl iodide consumed was recovered as iodide, possibly due to its oxidation to iodide which is the most prevalent form of iodine in natural waters. However, no additional iodide was detected after chemical reduction with ascorbate. For example, the value of accumulated iodide was 316 µmoles at the end of incubation while after reduction the value was 290 µmoles.

Strain IMB-1 also grows with glucose or acetate as electron donors. One-carbon compounds which support growth include mono-, di- and triethylamine, but no growth occurred with methanol or formate (see Table 1 below). Pyruvate supported growth, but no succinate, fumarate or citrate, while weak growth was obtained on malate (Table 1).

TABLE 1

| SUBSTRATE (mM) | $A_{680}$[a] |
| --- | --- |
| Trimethylamine (5 mM) | 0.230 |
| Dimethylamine (5 mM) | 0.190 |
| Monomethylamine (5 mM) | 0.095 |
| Pyruvate (5 mM) | 0.230 |
| Malate (5 mM) | 0.050 |
| Succinate (5 mM) | 0.005 |
| Citrate (5 mM) | 0.000 |
| Fumarate (5 mM) | 0.010 |
| Formate (5 mM) | 0.010 |
| Methanol (0.1 mM)[b] | 0.005 |
| NONE | 0.000 |

[a]incubation period = 66 hrs.
[b]no growth was obtained at higher concentrations of methanol In addition to MeBr and methyl iodide, growth was also obtained on methyl chloride, but no growth occurred on methyl fluoride or methane (See Table 2 below). Methyl fluoride (2–22 µmol/tube added) did not affect uptake of MeBr or growth of IMB-1 on MeBr. Growth on glucose, acetate, and methylamines was much more rapid than on the methyl halides, and also achieved higher cell densities. Strain IMB-1 was unable to grow without the provision of ammonium salts in the medium.

TABLE 2

| SUBSTRATE[a] (mmoles/L) | $\mu(H^{-1})$[b] | $Y_M$(g mol$^{-1}$) | MeBr oxidized (pmol/10$^6$ cells/h) |
| --- | --- | --- | --- |
| MeBr (0.8) | 0.03 | 4.2 | 1.4 |
| MeCl (0.8) | 0.03 | 3.4 | 1.7 |
| MeI (0.3) | 0.07 | 2.7 | 2.4 |
| MeF (0.4) | 0.00 | 0.0 | 0.0 |
| Methane (3.7) | 0.00 | 0.0 | 0.0 |
| MMA (5.0) | 0.17 | ND | 1.0 |
| DMA (4.0) | 0.19 | ND[c] | 1.1 |
| TMA (4.0) | 0.16 | ND | 0.8 |
| Glucose (2.0) | 0.24 | 30.0 | 0.6 |
| Acetate (5.0) | 0.24 | 5.1 | 0.8 |

[a]MeCl, MeI, and MeF refer to methyl chloride, methyl iodide, and methyl fluoride, and MA, DMA, and TMA refer to mono-, di-, and trimethylamine.
[b]specific growth rate = $\mu$
[c]ND = not determined Cells suspensions readily oxidized $^{14}$C-MeBr to $^{14}$CO$_2$ after two consecutive transfers in medium in which the growth substrate was not a methyl halide. Thus, the ability of strain IMB-1 to oxidize MeBr was present regardless of the substrate that was utilized for growth (see Table 2 above). However, MeBr oxidation rates in methyl halide-grown cells were significantly higher than in cells grown on methylated amines, glucose or acetate. The addition of methyl iodide to cells grown on methylamine initially retarded growth, resulting in a lag during which time methyl iodide was consumed. Cell suspensions harvested from these treatments all had equivalent capacity to oxidize $^{14}$C-MeBr regardless of whether or not they were exposed to methyl iodide. When normalized for cell densities, the rate of MeBr oxidation (pmol/10$^6$ cells/h) was: 1.2, 1.4, 1.1, 1.1, and 1.4 for cultures incubated with 0, 2, 5, 8 and 10 µmoles MeI, respectively. Similar results were obtained when acetate or glucose were used as the electron donor instead of methylamine.

Chloropicrin usually comprises about one third of the MeBr fumigation mixture injected into soils, and is used to enhance the overall biocidal effects of the mixture and to act as a warning agent to workers. Chloropicrin had a pronounced inhibitory effect upon growth in the experiments referred to above when applied at ≧0.05 µmol/tube regardless of what growth substrate was present. However, little or no inhibition was observed at the lowest chloropicrin application (0.005 µmol/tube). High concentrations of chloropicrin also caused substantial, but not complete, inhibition of $^{14}$C-MeBr oxidation by washed cell suspensions (see Table 3 below). It was concluded that lower levels of chloropicrin in the fumigant mixtures will result in enhanced MeBr biodegradation without compromising its role as a warning agent.

TABLE 3

Effect of chloropicrin on the oxidation of $^{14}$C—MeBr to $^{14}$C—CO$_2$ by cell suspensions of methylamine-grown IMB-1[a].

| CHLOROPICRIN[b] | $^{14}$CO$_2$ FORMED (nCi) | % INHIBITION |
| --- | --- | --- |
| NONE | 0.65 | 0 |
| 0.01 | 0.40 | 38 |
| 0.05 | 0.16 | 76 |
| 0.50 | 0.08 | 88 |
| 5.00[c] | 0.09 | 86 |

[a]Cells were incubated 2 h with 1.55 nCi $^{14}$C—MeBr and chloropicrin before being acidified.
[b]µmoles added per tube
[c]equivalent to 0.5 mM

EXAMPLE

In soil experiments, soils from a fumigated strawberry field located near Irvine, CA were employed. Soils (5 g) were placed in serum vials (27 ml), sealed under air with butyl rubber stoppers and injected with 0.2 ml of MeBr. In one experiment, soils received 0.5 ml of washed cell suspensions of either MeBr-grown or glucose-grown strain IMB-1. Live soil controls without added cells received only 0.5 ml of mineral salts medium, and a soil sample was autoclaved to serve as a killed control. In a second experiment, conditions were as above except that some soils were pretreated by receiving an injection of 75 µl of a 10% solution of methyl iodide (MeI), or of MeI plus 100 µl of 5 mM trimethylamine. After a pretreatment period lasting a few days (during which time the gas phase was analyzed for MeI) stoppers were removed and samples flushed with a stream of air for~10 minutes to remove any residual MeI. Samples were resealed and injected with 0.2 ml MeBr. All samples were incubated statically in the dark at~20° C.

In these experiments where live cell suspensions of IMB-1 were added to agricultural soils, all of the MeBr was consumed within 1–2 days depending upon whether cells were precultured on MeBr or on glucose. In contrast, bacteria in the uninoculated soils required nearly 1 week to oxidize the MeBr, while only a minor amount of chemical degradation occurred in heat-killed controls over this period. Live soils degraded low concentrations of methyl iodide after several days of pretreatment incubation while killed controls had only a minor amount of methyl iodide loss. When these pre-treated soils were exposed to MeBr, there was a rapid degradation of the MeBr relative to the live soils which did not receive pretreatment. Soils preincubated with trimethylamine as well as methyl iodide exhibited slightly more rapid rates of MeBr degradation.

Although methyl bromide can be oxidized by methane-oxidizing bacteria as well as by ammonia-oxidizing nitrifiers via the monooxygenases of the organisms, neither methanotrophs nor nitrifiers can use MeBr as a substrate to support growth. Thus, the ability of strain IMB-1 to achieve growth on MeBr is unique. Previous results with methyl fluoride have suggested that a non-methanotrophic component of the flora of methane-oxidizing soils oxidized MeBr in the presence of this inhibitor. Since methyl fluoride is not metabolized by strain IMB-1 (see Table 2 above) and has no effect on its ability to grow on or oxidize MeBr, it appears that organisms like IMB-1 were responsible for the consumption of MeBr in soils which was not linked to methanotrophs or nitrifiers.

Several facultative methylotrophs including strains of *Hyphomicrobium sp.* and *Methylobacterium extorquens* have been isolated which can grow on methyl chloride (6, 7), but they are not phylogenetically related to strain IMB-1. Since strain IMB-1 does not grow on methane, but does grow on other methyl halides (with the notable exception of methyl fluoride), methylamines, glucose, acetate, and pyruvate, strain IMB-1 is clearly a facultative methylotroph (see, e.g., Tables 1 and 2). In this respect, strain IMB-1 shares some superficial substrate affinities with the facultative methylotrophs isolated from Russian soils, as well as with strain ER2, a facultative methylotroph which degrades N-methyl carbamates. In this case, however, the two strains are closely related phylogenetically. Both strain ER2 and IMB-1 class in the Rhizobium clade of the Alpha subgroup of the Proteobacteria, which consists of aerobes noted for their ability to fix atmospheric nitrogen either independently or when in symbiosis with plants. Although strain IMB-1 was unable to grow without combined nitrogen under an air atmosphere, this result does not totally eliminate the possibility that it is capable of fixing nitrogen under other physiological conditions. The presence of nif genes in IMB-1 is currently being pursued to answer this question.

The ability of cells to oxidize MeBr was constitutive in strain IMB-1, regardless of whether it was grown on methyl halides or on glucose, acetate, or methylamines (see, e.g., Table 2). Therefore, it should be possible to mass culture strain IMB-1 on a conventional substrate and still be able to degrade MeBr, so as to eliminate the problem of having to employ a hazardous toxicant like MeBr as a substrate. When normalized for cell densities, cells grown on methyl halides had higher MeBr oxidation activity than those which were grown on other substrates (Table 2). Cells grown on conventional substrates in the presence of trace levels of methyl iodide did not induce higher MeBr oxidation activity in cell suspensions. Although cells were able to oxidize the methyl iodide, they did not achieve any greater capacity to oxidize MeBr after they were grown out on methylamine, glucose, or acetate.

As discussed above, it has been found that the addition of live cells to soils greatly speeded their ability to consume MeBr and thus seeding soils with live cells of mass-cultured IMB-1 should enhance the biodegradation of MeBr during fumigation of agricultural fields. It is noted that tarped periods of fumigation usually last for several days, but in contrast, the IMB-1 enhanced oxidation of fumigation-levels of MeBr was so rapid (1–2 days) as to raise concern that insufficient levels of fumigant would be present over the course of the tarping period to effectively eliminate target pests. One practical solution to this problem could be to seed only the surface soils (e.g., upper 5 cm.) with bacteria just prior to the soils being covered by tarps. This would create a zone of intense bacterial MeBr degradation at the surface of the soil which would intercept the upward flux of MeBr from its deeper injection depth.

Another approach would be to pretreat fields with methyl iodide, a substance which has been proposed as an alternative "ozone-safe" fumigant in the event that MeBr use is eliminated by a worldwide ban. Because IMB-1 also grows on methyl iodide (see, e.g., Table 2), such an approach would also increase the cell population of these organisms in the soil and speed the overall rate of MeBr biodegradation during fumigation operations. Experimental results with soils indicate that such an approach is feasible.

One method of cultivating the strain IMB-1 is to use the mineral salts medium of Doronina et al. (see Doronina, N. V., A. P. Sokolov, and Y. A. Trotsenko, Isolation and Initial Characterization of Aerobic Chloromethane-utilizing Bacteria. FEMS Microbial. Lett 142 (1996): pp. 179–183.) as modified by Miller et al. (see Connell, T. L., S. B. Joye, L. G. Miller, and R. S. Oremland, Bacterial Oxidation of Methyl Bromide in Mono Lake, Calif., Environ. Sci. Technol. 31 (1997): pp. 1489–1495.). In this method, cells were grown in crimp-seal "Balch" tubes filled with 10 ml of medium and sealed with a 15 ml air headspace. Substrates were added by syringe injection and those tested for growth included methyl bromide, methyl iodide, methyl chloride, methyl fluoride, methane, Na formate, methanol, monomethylamine, dimethylamine, trimethylamine, Na acetate, glucose, sodium pyruvate, sodium citrate, sodium malate, and succinic acid. The pH was adjusted to 7.2, and after autoclaving, tubest were incubated at 30° C. with constant reciprocal shaking. Molar growth yield ($Y_m$) values were obtained by dividing the amount of substrate consumed into the final cell density achieved, assuming that the cell dry weight was $3.4\times10^{-11}$ mg/cell for the IMB-1 isolate.

A MeBr oxidation assay was conducted on washed cell suspensions after cells were taken through two successive transfers on the substrate indicated. Ten ml of cells from the growth tubes were centrifuged (10,000×g for 15 min. at 7° C.) and washed twice with mineral salts medium. The final pellets were resuspended in 5 ml of mineral salts medium, placed in 13 ml serum bottles and sealed with crimped butyl rubber stoppers. $^{14}$C-MeBr (1.0–2.0 $\mu$Ci/bottle; specific activity=29.7 mCi/mmole; purity=100%; new England Nuclear, Boston, Mass.) was injected and cells were incubated statically for 4–6 h, at which time 0.25 ml 6 N HCl was injected to stop the reaction and liberate $^{14}CO_2$ into the gas phase. Tubes were vigorously hand shaken for 5 minutes before the gas phase was sampled for analysis.

In another series of experiments, varying trace levels of methyl iodide (MeI) were added to cells growing on glucose, methylamine, or acetate in determining that, as discussed above, pre-exposure to MeI increases the ability of harvested cell suspensions to oxidize $^{14}$C-MeBr.

It is noted that the complete sequence of the 16S rRNA gene from IMB-1 has been deposited in the GenBank database under accession no. AF034798.

In brief summary, the application of bacteria from agricultural soils, such as those discussed above, through e.g., the application of freeze-dried bacterial cells to soils during fumigation, enhances the oxidation of MeBr during fumigation events. The amount of chloropicrin employed in the fumigant should be lowered, and pre-treatment of soils with of methyl iodide enhances the oxidation effect. The bacteria can be mass-cultured using glucose or a less-expensive substrate like methylamine.

Although the present invention has been described to specific exemplary embodiments thereof, it will be understood by those skilled in the art that variations and modifications can be effected in these exemplary embodiments without departing from the scope and spirit of the invention.

What is claimed:

1. A method for enhancing oxidation of methyl bromide during agricultural fumigations of fields of plants growing in soil using a fumigant containing methyl bromide, said method comprising adding a methylotrophic bacterium, wherein said bacterium comprises a 16S ribosomal RNA gene sequence in the Alpha subgroup of Proteobacteria designated strain IMB-1 having the accession number ATCC 202197, to the soil in an amount effective to provide bacterial oxidation of the methyl bromide.

2. A method as claimed in claim 1 wherein said bacterium comprises a bacterium isolated from agricultural soil.

3. A method as claimed in claim 1 wherein said fumigant includes chloropicrin in an amount reduced to a level which permits said bacterial oxidation and which still enables the chloropicrin to serve as a warning agent for excessive release of methyl bromide from the soil.

4. A method as claimed in claim 1 wherein the soil is pretreated with methyl iodide.

5. A method as claimed in claim 1 wherein said bacterium is applied to the soil as freeze-dried bacterial cells during the fumigation.

6. A method as claimed in claim 1 wherein said bacterium is prepared by mass culturing.

7. A method as claimed in claim 6 wherein said mass culturing uses glucose as a substrate.

8. A method as claimed in claim 6 wherein said mass culturing uses methylamine as a substrate.

* * * * *